United States Patent [19]

Gipson

[11] Patent Number: 4,919,156
[45] Date of Patent: Apr. 24, 1990

[54] COMBINATION DENTAL DEVICE

[76] Inventor: Samuel D. Gipson, 2344 Park Ave., Memphis, Tenn. 38114

[21] Appl. No.: 351,535

[22] Filed: May 15, 1989

[51] Int. Cl.⁵ .......................................... A45D 44/18
[52] U.S. Cl. ................................. 132/309; 132/311; 132/324
[58] Field of Search ............... 132/324, 325, 308, 309, 132/311, 321, 328

[56] References Cited

U.S. PATENT DOCUMENTS

| | | | |
|---|---|---|---|
| 1,473,766 | 11/1923 | Healy | 132/309 |
| 1,816,092 | 7/1931 | Schmitter | 132/309 |
| 2,370,005 | 2/1945 | Brown | 132/308 |
| 2,601,244 | 6/1952 | Boulicault | 132/309 |
| 2,640,488 | 6/1953 | Velodota | 132/308 |
| 2,980,119 | 4/1961 | Rebstock | 132/308 |
| 3,782,397 | 1/1974 | McCord | 132/309 |
| 4,408,920 | 10/1983 | Walther et al. | 132/325 X |
| 4,527,574 | 7/1985 | Manfredi | 132/308 |
| 4,821,752 | 4/1989 | Widlak | 132/324 X |

Primary Examiner—Robert P. Swiatek
Assistant Examiner—Nicholas D. Lucchesi
Attorney, Agent, or Firm—John J. Mulrooney

[57] ABSTRACT

A combination dental device has a fountain pen type housing for a toothbrush, refillable toothpaste cartridge, dental floss dispenser and cutter, and a retractable gum stimulator. The dental fixtures and supplies are replaceable whereby the housing may be permanent of reusable.

1 Claim, 1 Drawing Sheet

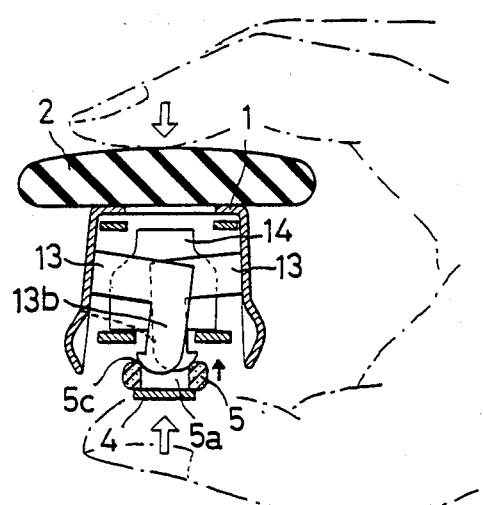
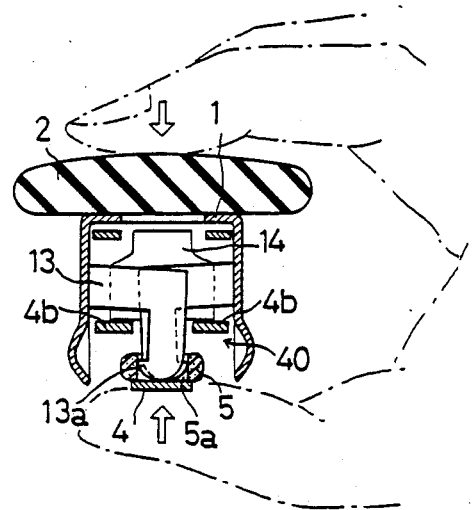
FIG. 6    FIG. 7
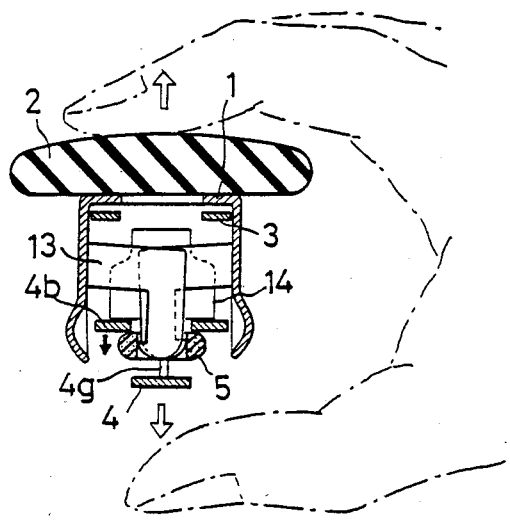
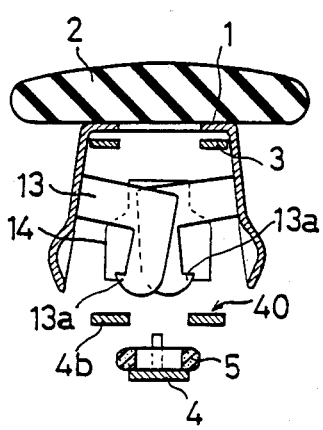
FIG. 8    FIG. 9

COMBINATION DENTAL DEVICE

BACKGROUND OF THE INVENTION

This invention relates to a COMBINATION DENTAL DEVICE, and more particularly to a complete dental device which combines in a single, portable housing a toothbrush, a toothpaste cartridge, a supply of dental floss, and a gum stimulator.

The importance of good dental hygiene, including the proper care of the teeth by daily brushing and cleaning of the teeth after each meal, and daily stimulation of the gums, is well-recognized. Such recommended care ordinarily cannot be given to the teeth by most persons because the necessary dental implements and supplies, such as the toothbrush, toothpaste, dental floss and gum stimulator are not ordinarily carried, or otherwise are not conveniently available or accessible throughout the day. The prior art contains some combination dental devices. See, for example, U.S. Pat. Nos. 2,736,917: 3,782,397: and 3,890,986. However, none of the above patents, or any devices known to the inventor, disclose a fountain pen type container, including a toothbrush, a dentifrice supply a dental floss dispenser and a retractable interdental gum stimulator in a single housing. Nor do any of the known devices combine the dental elements and supplies in the simple and novel design disclosed by the present invention.

Therefore, an object of the invention is to provide a new and improved combination dental device.

Another object of the invention is to provide an improved combination dental device that comprises a total dental kit including a toothbrush, toothpaste, dental floss and gum stimulator.

Another object of the invention is to provide a complete dental device having a novel design and shape in the form of a fountain pen type housing.

Another object of the invention is to provide a complete dental device having a retractable gum stimulator.

Another object of the invention is to provide a complete dental device having replaceable elements.

Another object of the invention is to provide a complete dental device designed in a compact and sturdy manner in the approximate size of a toothbrush so that it may be conveniently carried in the pocket or purse.

SUMMARY OF THE INVENTION

The new and improved COMBINATION DENTAL DEVICE of the present invention comprises a plastic housing molded in the approximate shape of a fountain pen, and having mounted therein a toothbrush at one end covered by a removeable cap having a pocket clip thereon; a spool of dental floss accessible through a hole in the housing and a cutter for cutting said dental floss; a refillable cartridge of toothpaste within said housing: and a retractable interdental gum stimulator positioned at the other end of said housing.

DESCRIPTION OF THE PREFERRED EMBODIMENT

Figure 1:
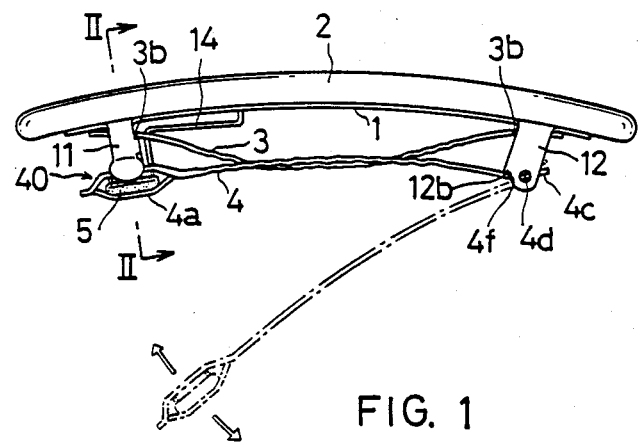
FIG. 1 is a front elevational view of the dental device of the present invention.

Referring to the drawings, the combination dental device of the present invention is generally designated by the reference numeral 10. The device comprises a molded plastic housing having the general shape and size of a fountain pen, and includes a removable cap 12, a cylindrical body or housing comprising a top section 14, a bottom section 16, which is separable from said top section 14, and a bottom or end closure part 18.

The cap 12 has a pocket clip 20 thereon to permit the dental device to be securely carried in a shirt pocket and a plurality of air ventilation holes 13 therein to allow the toothbrush 22 to dry after use.

The cap 12 is removable to expose a conventional toothbrush 22 having the usual bristles 23 and handle 24 thereon. The handle 24 is securely but removably mounted in housing section 14 to provide the rigidity needed for brushing teeth, yet to permit the toothbrush to be removed and replaced as needed. Such mounting means are well-known to those skilled in the art.

Top housing section 14 and bottom housing section 16 are separate elements as shown in the drawing. A sleeve 27 is integral with top section 14 and extends downwardly into bottom section 16 and provides a friction type fit between top section 14 and bottom section 16. A toothpaste cartridge 26 fits within the sleeve 27. A tube or cartridge 26 useful for a supply of toothpaste or other dentifrice is snuggly carried partly in top housing 14 and partly in bottom housing 16. One end of cartridge 26 has a opening 28 and a cap or plug 30 for closing opening 28. The other end of cartridge 26 has another opening 32 and a cap 34 therefor. The opening 28 is to permit toothpaste or other dentifrice to be admitted to the cartridge 26 and the opening 32 is to permit the toothpaste to be extruded onto the brush 22.

A dental floss spool or dispenser 36 is rotatably mounted in top housing section 14. A supply of dental floss 38 on spool 36 has an end which extends through an opening 15 in top housing section 14 and may be cut on a floss cutter 40 mounted on housing section 14. A flap or door 35 in top housing 14 permits the dental floss supply to be renewed. An alternative to the flap or door 35 shown in the drawing would be to omit the door 35 and load the dental floss dispenser 38 into top section 14 through the top opening therein where the handle 24 of toothbrush 22 fits.

A gum stimulator 19 is an integral part of the cap 18 which fits on the bottom of the housing 10. The gum stimulator is retractable so that when not in use it fits within the lower housing 16, but may be removed and fit within the bottom housing as shown for use.

It will thus be seen that the present invention provides a complete combination dental device which is novel, convenient, simple, efficient, and practical to use, all within a single housing which is the approximate size and shape of a fountain pen. The complete dental device of the present invention permits a person who may be travelling or otherwise away from home and without the usual dental equipment and supplies to provide for complete dental hygiene by brushing, flossing, and stimulating the gums.

What I claim is:

1. A combination dental device having a toothbrush, a dental floss supply and dispenser, a dentifrice supply and dispenser, and an interdental gum stimulator all within a structure resembling a traditional fountain pen case, said dental device comprising:

a removable cap having a pocket clip thereon and ventilation holes therein;

an upper cylindrical section having a top end adapted to receive said removable cap; a bottom end; an integral sleeve therein which extends from a point within said upper cylindrical section to below said bottom end; an aperture and a door therefor permitting access to the interior of said upper cylindrical section; a hole adjacent said aperture; and a dental floss cutter mounted on said upper cylindrical section adjacent said aperture and said hole;

a toothbrush having bristles mounted at one end of a handle; said handle being mounted in said top end of are exposed at said top end and fit within said removable cap when said removable cap is positioned on said top end of said upper cylindrical section;

a dental floss dispenser having a supply of dental floss thereon rotatably mounted in said upper cylindrical section adjacent said aperture therein, whereby said dental floss may be threaded through said hole and cut on said cutter;

a cartridge for a supply of dentifrice, said cartridge having a cylindrical shape and being designed to fit within said sleeve in said upper cylindrical section whereby said cartridge when positioned in said sleeve is partly within and partly without said sleeve; said cartridge having a first opening and a cap therefor at one end to permit dentifrice to be admitted and a second opening and cap therefor at the other end to permit said dentifrice to be applied to said toothbrush;

a lower cylindrical section having a top end and a bottom end, said top end of said lower cylindrical section being designed to receive and form a releasable friction connection to said sleeve, whereby said dentifrice cartridge partly positioned in said sleeve extends into said lower cylindrical section;

an elongated closure element having a flat surface at one end thereof and an interdental gum stimulator at the other end thereof, said closure element being capable of fitting within said bottom end of said lower cylindrical section is either of two positions, a first position whereby said flat surface faces outwardly from said lower cylindrical section and said interdental gum stimulator faces inwardly thereto and is concealed within said lower cylindrical section, and a second position whereby said flat surface faces inwardly and said interdental gum stimulator faces outwardly from said lower cylindrical section.

* * * * *

UNITED STATES PATENT AND TRADEMARK OFFICE
CERTIFICATE OF CORRECTION

PATENT NO. : 4,919,156

DATED : April 24, 1990

INVENTOR(S) : Samuel D. Gipson

It is certified that error appears in the above-identified patent and that said Letters Patent is hereby corrected as shown below:

The title page should be deleted to appear as per attached title page.

Figure 2:
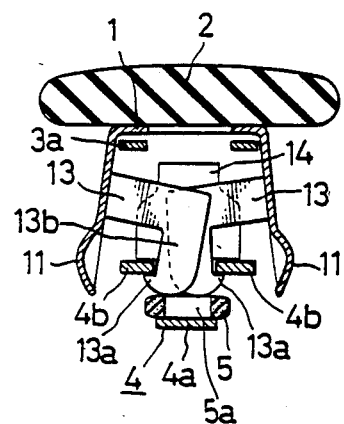
FIG. 2 is an exploded view of the dental device.
Figure 3:
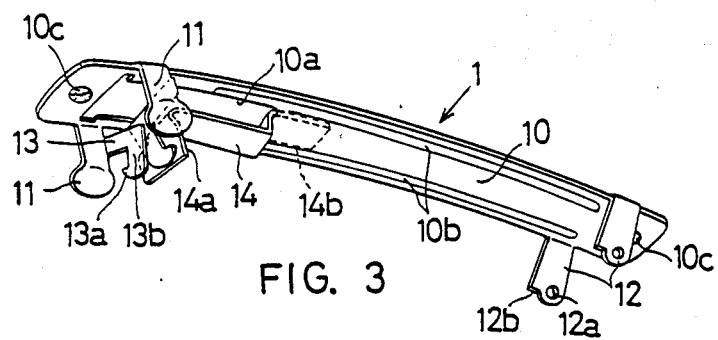
FIG. 3 is a perspective view of the dental device.
Figure 4:
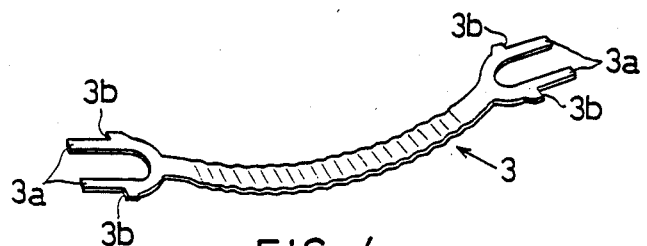
FIG. 4 is an elevational view of the toothpaste cartridge.
Figure 5:
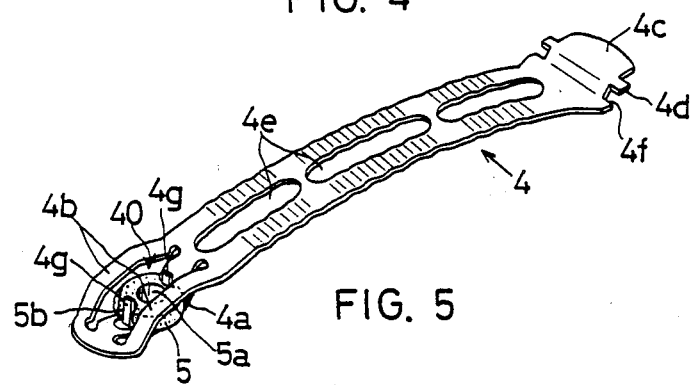

The sheets of drawings consisting of figures 1-9 should be deleted to appear as per attached sheet.

Signed and Sealed this

Twenty-first Day of August, 1990

Attest:

HARRY F. MANBECK, JR.

Attesting Officer   Commissioner of Patents and Trademarks

United States Patent [19]

Gipson

[11] Patent Number: 4,919,156
[45] Date of Patent: Apr. 24, 1990

[54] COMBINATION DENTAL DEVICE

[76] Inventor: Samuel D. Gipson, 2344 Park Ave., Memphis, Tenn. 38114

[21] Appl. No.: 351,535

[22] Filed: May 15, 1989

[51] Int. Cl.⁵ .............................................. A45D 44/18
[52] U.S. Cl. ...................................... 132/309; 132/311; 132/324
[58] Field of Search ............... 132/324, 325, 308, 309, 132/311, 321, 328

[56] References Cited

U.S. PATENT DOCUMENTS

| | | | |
|---|---|---|---|
| 1,473,766 | 11/1923 | Healy | 132/309 |
| 1,816,092 | 7/1931 | Schmitter | 132/309 |
| 2,370,005 | 2/1945 | Brown | 132/308 |
| 2,601,244 | 6/1952 | Boulicault | 132/309 |
| 2,640,488 | 6/1953 | Velodota | 132/308 |
| 2,980,119 | 4/1961 | Rebstock | 132/308 |
| 3,782,397 | 1/1974 | McCord | 132/309 |
| 4,408,920 | 10/1983 | Walther et al. | 132/325 X |
| 4,527,574 | 7/1985 | Manfredi | 132/308 |
| 4,821,752 | 4/1989 | Widlak | 132/324 X |

Primary Examiner—Robert P. Swiatek
Assistant Examiner—Nicholas D. Lucchesi
Attorney, Agent, or Firm—John J. Mulrooney

[57] ABSTRACT

A combination dental device has a fountain pen type housing for a toothbrush, refillable toothpaste cartridge, dental floss dispenser and cutter, and a retractable gum stimulator. The dental fixtures and supplies are replaceable whereby the housing may be permanent of reusable.

1 Claim, 1 Drawing Sheet

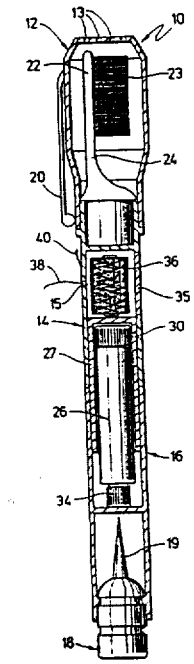

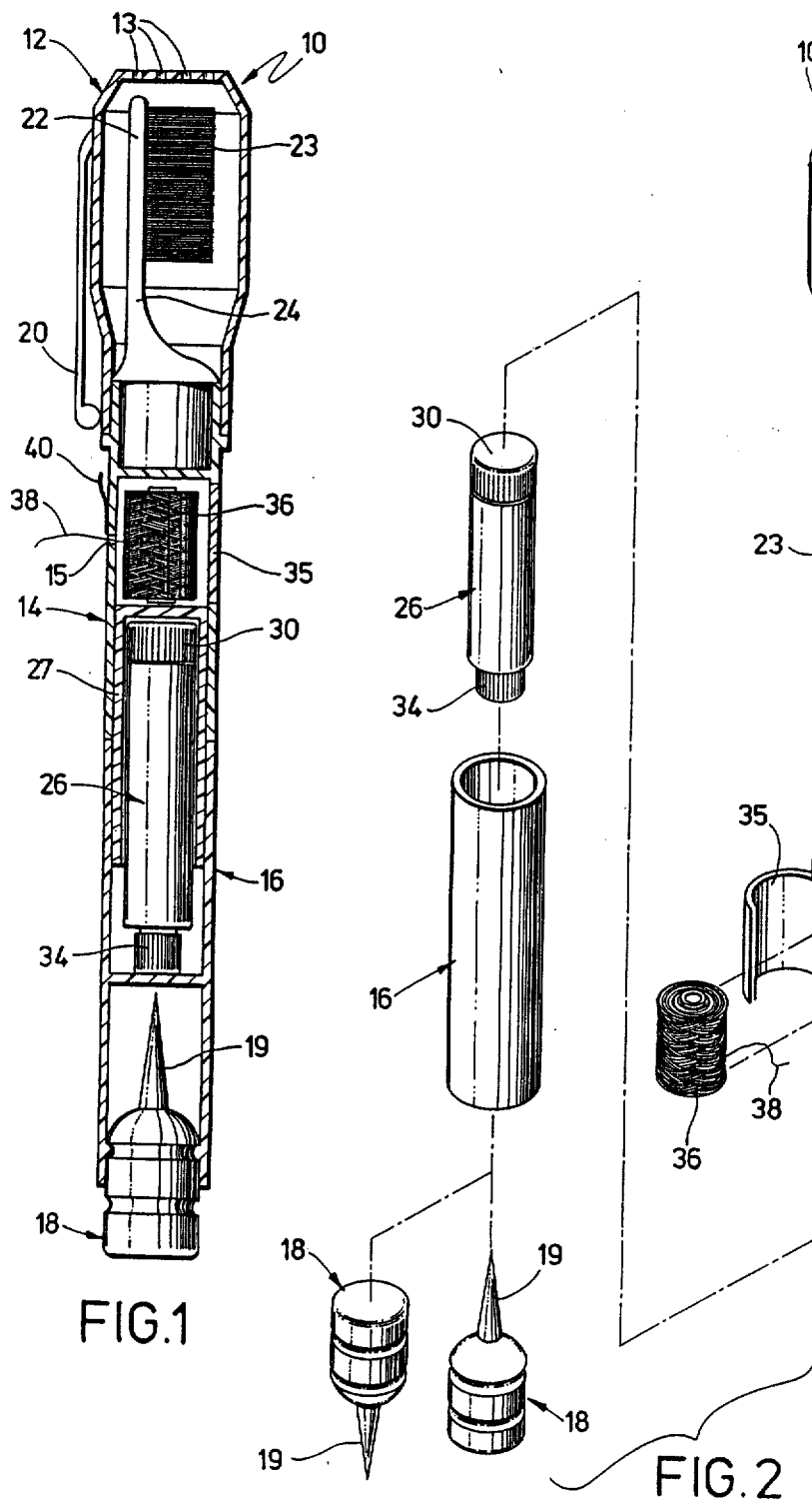
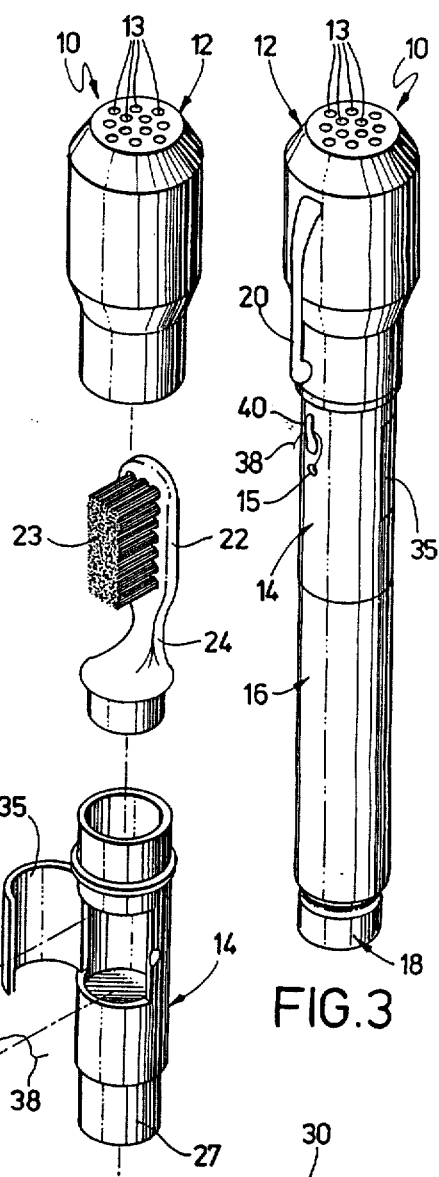
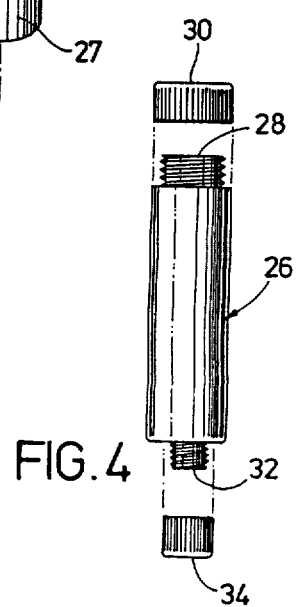
FIG.1
FIG.2
FIG.3
FIG.4